US007087046B2

(12) United States Patent
Van Gompel et al.

(10) Patent No.: US 7,087,046 B2
(45) Date of Patent: Aug. 8, 2006

(54) ABSORBENT GARMENT WITH REFASTENABLE ADHESIVE ELEMENTS ENGAGING AN ELONGATABLE BODY PANEL AND METHODS FOR THE USE AND MANUFACTURE THEREOF

(75) Inventors: Paul T. Van Gompel, Hortonville, WI (US); Jacqueline A. Gross, Neenah, WI (US); Yung H. Huang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 494 days.

(21) Appl. No.: 10/238,202

(22) Filed: Sep. 9, 2002

(65) Prior Publication Data

US 2004/0049168 A1    Mar. 11, 2004

(51) Int. Cl.
*A61F 13/20* (2006.01)
(52) U.S. Cl. ............................ 604/385.22; 604/385.22; 604/389
(58) Field of Classification Search ........... 604/385.22, 604/389
See application file for complete search history.

(56) References Cited

U.S. PATENT DOCUMENTS

| 4,761,318 A | 8/1988 | Ott et al. |
| 5,019,065 A | 5/1991 | Scripps |
| 5,032,122 A | 7/1991 | Noel et al. |
| 5,061,262 A * | 10/1991 | Chen et al. ............. 604/389 |
| 5,147,347 A | 9/1992 | Huang et al. |
| 5,151,092 A | 9/1992 | Buell et al. |
| 5,399,177 A | 3/1995 | Blaney et al. |
| 5,542,942 A | 8/1996 | Kline et al. |
| 5,547,531 A | 8/1996 | Allen et al. |
| 5,549,591 A | 8/1996 | Landvogt |
| 5,595,567 A | 1/1997 | King et al. |
| 5,615,460 A | 4/1997 | Weirich et al. |
| 5,624,427 A | 4/1997 | Bergman et al. |
| 5,647,864 A | 7/1997 | Allen et al. |
| 5,681,306 A | 10/1997 | Goulait et al. |
| 5,888,607 A | 3/1999 | Seth et al. |
| 5,968,031 A | 10/1999 | Schmitz |
| 6,063,466 A | 5/2000 | Tuschy et al. |

(Continued)

FOREIGN PATENT DOCUMENTS

DE    37 10 037 A1    10/1988

(Continued)

OTHER PUBLICATIONS

International Search Report in International Application No. PCT/US03/15012, dated Sep. 9, 2003, 8 pages.

*Primary Examiner*—Tatyana Zalukaeva
*Assistant Examiner*—Ginger Chapman
(74) *Attorney, Agent, or Firm*—Brinks, Hofer, Gilson & Lione (57) ABSTRACT

An absorbent garment includes a body panel comprising a liquid permeable, non-woven material. The non-woven material is elastically gathered and is elongatable between a non-elongated condition and an elongated condition in response to an application of a tensile force. Preferably, the body panel is elongatable at least 75% between the non-elongated condition and the elongated condition upon the application of the tensile force. A fastener includes an adhesive that releasably engages the elastically gathered non-woven material. The fastener is releasably disengageable from the body panel in response to an application of a disengaging shear force. Preferably, the disengaging shear force is greater than the tensile force. Methods for manufacturing and using the absorbent garment are also provided.

16 Claims, 6 Drawing Sheets

U.S. PATENT DOCUMENTS

| | | | |
|---|---|---|---|
| 6,387,085 B1 | 5/2002 | Van Gompel et al. | |
| 2002/0040214 A1 | 4/2002 | Holmquist | |
| 2005/0203472 A1* | 9/2005 | Sakaguchi et al. | 604/367 |

FOREIGN PATENT DOCUMENTS

| EP | 0 252 413 B1 | 11/1991 |
|---|---|---|
| EP | 0 289 198 B1 | 2/1992 |
| EP | 0 609 340 B1 | 9/1996 |
| EP | 0 495 516 B1 | 4/1998 |
| EP | 0 714 351 B1 | 12/1998 |
| EP | 1 092 759 A2 | 4/2001 |
| GB | 2 080 093 A | 2/1982 |
| WO | WO 97/25892 | 7/1997 |

* cited by examiner

ABSORBENT GARMENT WITH REFASTENABLE ADHESIVE ELEMENTS ENGAGING AN ELONGATABLE BODY PANEL AND METHODS FOR THE USE AND MANUFACTURE THEREOF

BACKGROUND

The present invention relates generally to an absorbent garment, and in particular, to an absorbent garment having a refastenable adhesive element that releasably engages an elongateable panel and methods for the user and manufacture thereof.

Absorbent garments, and in particular disposable absorbent garments, can be configured in many different forms. For example, absorbent garments can be configured as a pant-type, pull-on garment, or as a diaper-type product that is drawn up between the legs and fastened about the waist with various fastening systems. These types of absorbent garments can be configured with fastening systems that allow the user to detach and reattach various fasteners so as to provide a refastenable absorbent garment. Often, the fastening system is configured with hook and loop elements or with adhesive elements. In either system, it is usually desirable to provide a landing material, or landing zone, to releasably engage the fastener.

The use of a landing material or zone is particularly desirable with adhesive fasteners, which can become easily contaminated by certain materials, thereby reducing their effectiveness after repeated applications. Many of the types of materials used as landing materials, such as films, however, are not breathable or stretchable and are not particularly comfortable next to the body of the user.

Moreover, it is often desirable to provide the absorbent garment with various elastic elements that can conform to the body of the user and provide a comfortable, snug fit. However, many types of landing materials suitable for adhesive-type fasteners are not well suited for stretching, and/or may interfere with the overall conformance of the garment to the body of the user.

SUMMARY

Briefly stated, in one preferred embodiment, an absorbent garment includes a body panel comprising a liquid permeable, non-woven material. The non-woven material is elastically gathered and is elongatable between a non-elongated condition and an elongated condition in response to an application of a tensile force. Preferably, the body panel is elongatable at least 75% between the non-elongated condition and the elongated condition upon the application of the tensile force. A fastener includes an adhesive that releasably engages the elastically gathered non-woven material. The fastener is releasably disengageable from the body panel in response to an application of a disengaging shear force. Preferably, the disengaging shear force, namely, the shear strength of the adhesive attachment, is greater than the tensile force needed to elongate the body panel during the normal use of the absorbent garment.

In another aspect, one preferred embodiment of a method of manufacturing an absorbent garment includes moving the body panel in a machine direction, wherein the body panel comprises a liquid penneable, non-woven material. The non-woven material is elastically gathered and is elongatable between a non-elongated condition and an elongated condition in response to an application of a tensile force. Preferably, the body panel is elongated at least 75% between the non-elongated condition and elongated condition upon said application of the tensile force. The method further includes releasably engaging the elastically gathered non-woven material of the body panel with an adhesive fastener. Preferably, the fastener is releasably disengageable from the body panel in response to an application of a disengaging shear force, wherein the shear force is preferably greater than the tensile force.

In yet another aspect, one preferred embodiment of a method of using an absorbent garment includes fitting a body panel comprising an elastically gathered, liquid permeable, non-woven material around a waist of a user. The body panel is preferably releasably engaged with a fastener comprising an adhesive releasably adhered to the elastically gathered, liquid permeable, non-woven material. The method further preferably includes elongating the body panel as the body panel is fitted around the waist of the user and thereby applying a tensile force to the body panel. The method further preferably includes maintaining the releasable adherance of the adhesive to the elastically gathered, liquid permeable, non-woven material while the tensile force is being applied to the body panel during the normal use of the absorbent garment.

The presently preferred embodiments provide significant advantages over other absorbent garments and methods for the use and manufacture thereof. For example, the liquid permeable, non-woven material of the body panel provides a breathable material that provides maximum comfort against the skin of the user. In addition, the elastically gathered non-woven material easily and effectively conforms to the body of the user. At the same time, the adhesive fastener can be releasably engaged with the gathered non-woven material. Since the disengaging shear force is preferably greater than the tensile force required to elongate the body panel, the body panel will elongate as it is fitted to the user, rather than disengaging the fastener from the body panel. At the same time, the adhesive is not as easily contaminated by the gathered material, due to the reduced surface area contact therewith. As such, an absorbent garment is provided that provides a repeatable and reliable fastening system in conjunction with a body-conforming body panel.

The foregoing paragraphs have been provided by way of general introduction, and are not intended to limit the scope of the following claims. The presently preferred embodiments, together with further objects and advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

DETAILED DESCRIPTION OF THE PRESENTLY PREFERRED EMBODIMENTS

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user. The terms "upper," "lower," "inner", and "outer" as used herein are intended to indicate the direction relative to the user wearing an absorbent garment over the crotch region, while the terms "inboard" and "outboard" refer to the directions relative to a centerline of the garment. For example, the terms "inner" and "upper" refer to a "bodyside," which means the side closest to the body of the user, while the terms "outer" and "lower" refer to a "garment side". The term "bodyside" should not be interpreted necessarily to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted necessarily to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

Referring to FIGS. 5–8, an absorbent garment 2 includes a first, front body panel 4 and a second, rear body panel 6. The first and second body panels each have an inner, bodyside surface 10 an outer, garment side surface 12 and a length, which is less the overall length of the absorbent garment. Each of the first and second body panels has a first and second longitudinally opposed terminal end edges 16, 14, 20, 18, and outer side edges, including a tapered edge 22, 26 and an outboard edge 24, 28 formed along the outer periphery of laterally opposed ear portions 30, 32. Alternatively, one or both of the front and rear body panels is configured without a tapered side edge, and instead is formed with a terminal end edge extending along the entire width of the body panel between the opposite outboard edges. Of course, it should be understood that the terminal edges can assume many shapes, including various scalloped or sinusoidal shapes.

Figure 5:
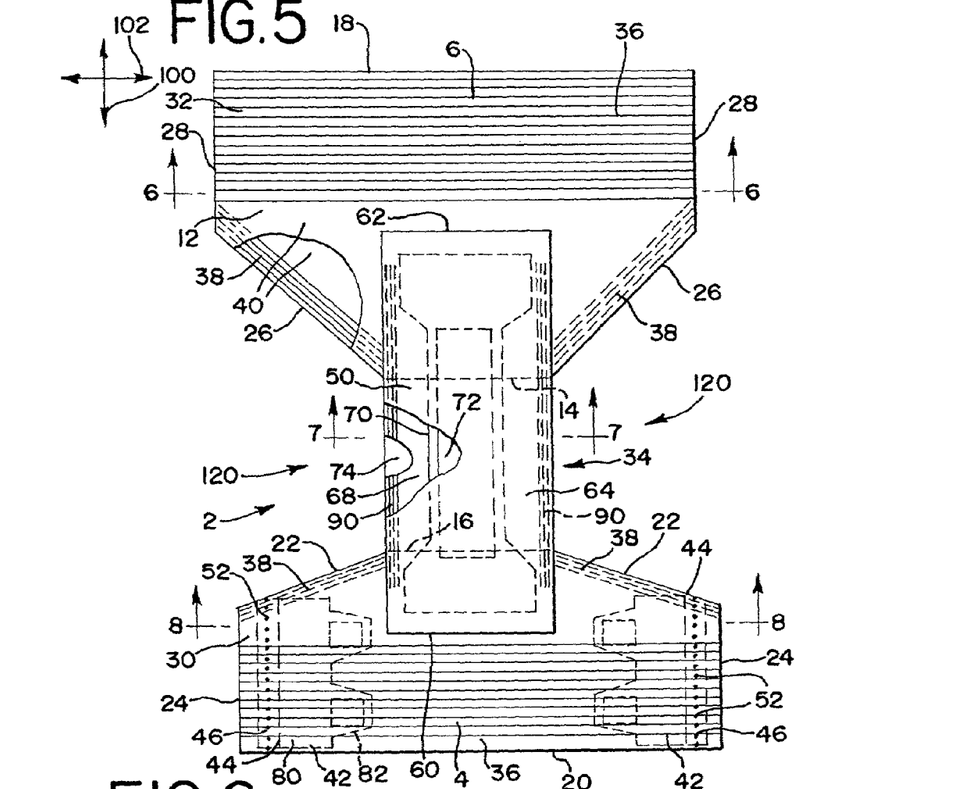
FIG. 5 is a plan view of a second embodiment of an absorbent garment taken from the bodyside thereof.

Referring to FIG. 5, the first terminal edges 16, 14 of the first and second body panels are longitudinally spaced to form an opening 34 or gap therebetween in the crotch region of the garment, while the second terminal edges 20, 18 of the first and second body panels are located proximate to and define front and back waist edges respectively. A plurality of, meaning two or more, laterally extending elastic elements 36 can be secured to each of the first and second body panels. Likewise, one or more leg elastic elements 38 can be secured along the tapered side edge of the body panels to form a gasket with the leg of the user. The various waist and leg elastic elements can be formed from rubber or other elastomeric materials. One suitable material is a LYCRA® elastic material. For example, the various elastic elements can be formed of LYCRA® XA Spandex 540, 740 or 940 detex T-127 or T-128 elastics available from E. I. duPont De Nemours and Company, having an office in Wilmington, Del.

Figures 6, 7, 8:
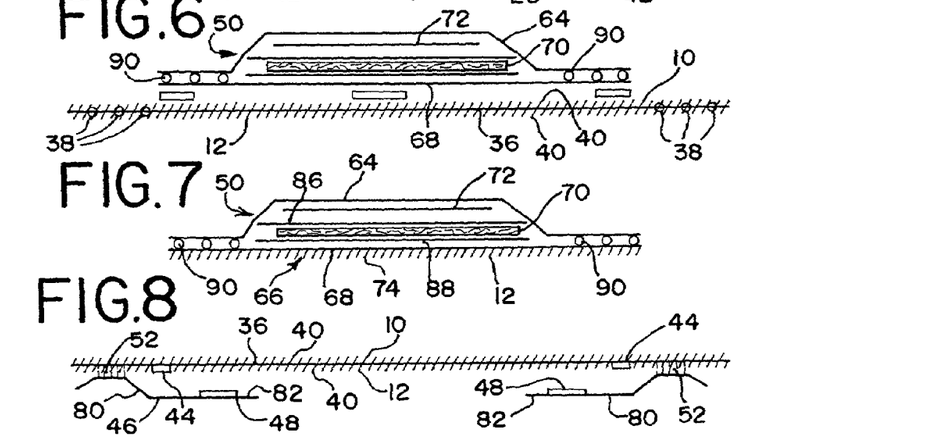
FIG. 6 is a schematic illustration of a cross-sectional view of the absorbent garment taken along line 6—6 in FIG. 5.
FIG. 7 is a schematic illustration of a cross-sectional view of the absorbent garment taken along line 7—7 in FIG. 5.
FIG. 8 is a schematic illustration of a cross-sectional view of the absorbent garment taken along line 8—8 in FIG. 5.

For example, as shown in FIGS. 5, 6 and 8, each panel can be made of an elasticized composite panel material comprising two non-woven substrates 40 with the plurality of elastic strands 38, 36 sandwiched therebetween. The elastic strands are positioned in the waist regions and along the leg perimeters. A portion of the leg elastic elements 38 can extend under a side portion of an absorbent composite 50. In one preferred embodiment, the elastic elements 36 are elongated to an unstable state prior to being secured between the substrates of the body panel. For example, the elastic elements can preferably be elongated between about 20% and about 300%, more preferably between about 50% and about 250% and even more preferably between about 100% and about 200%. The elastic elements 36 are then secured between the substrates and are allowed to relax to a stable state, thereby gathering the body panel 4, 6 material in a non-elongated condition. In other embodiments, the elastic elements are secured to one or more substrates without elongating the elastic elements, for example where the substrate is necked. The term "gather," and variations thereof, as used herein means puckered, or contracted into folds or wrinkles, which should be understood as including micro-pleats.

Preferably, in the embodiment of FIG. 5, the outboard edges 24, 28 of the front and rear body panels are connected, for example by bonding or sewing, to create a seam of a pant garment. When secured in this way, the body panels and absorbent composite define a pair of leg openings 120 on each side of the absorbent composite 50. Preferably, a pair of fasteners 42 are secured to the front body panel across a line of weakness 44, such as a perforation. In particular, the fasteners have a base 46 fixedly secured to the body panel 4 on an outboard side of the line of weakness 44. The base is fixed to the body panel along an attachment location 52 with adhesives, sonic bonds, thermal bonds, stitching, pinning, or other types of known fastening devices. The fasteners 42 bridge the line of weakness 44 and have an adhesive element 48 or zone that releasably engages the gathered body panel material on the opposite side of the line of weakness 44. Alternatively, the line of weakness can be formed for example along a breakable seam between the front and rear body panels, or along a length of one or both of the front and rear body panels, with the fastener bridging the line of weakness.

Figure 1:
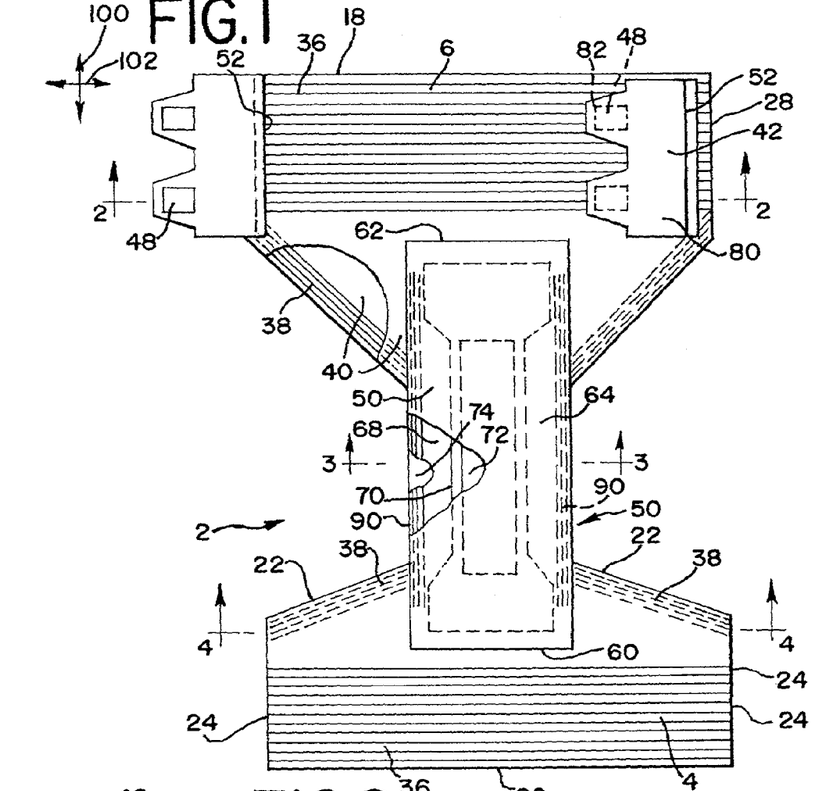
FIG. 1 is a plan view of a first embodiment of an absorbent garment taken from the bodyside thereof.
Figure 2:
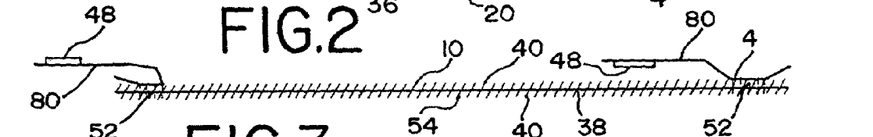
FIG. 2 is a schematic illustration of a cross-sectional view of the absorbent garment taken along line 2—2 in FIG. 1.
Figure 3:
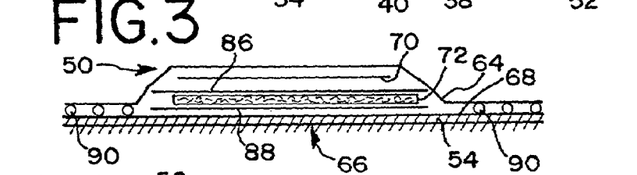
FIG. 3 is a schematic illustration of a cross-sectional view of the absorbent garment taken along line 3—3 in FIG. 1.
Figure 13:
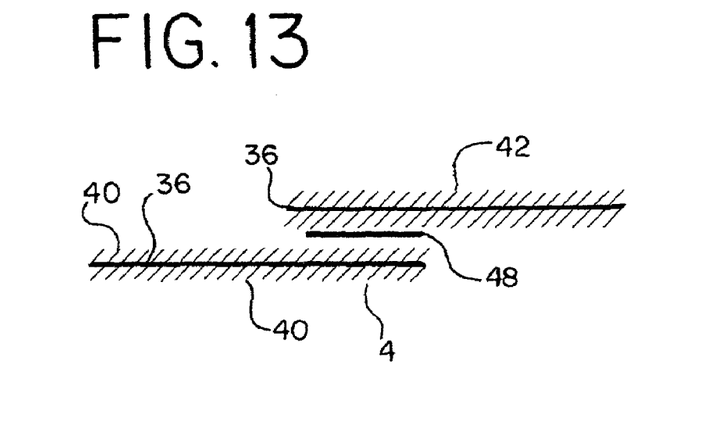
FIG. 13 is a cross-sectional view of an adhesive fastener releasably engaging an elastically gathered material.

Referring to FIG. 1, an alternative embodiment of the absorbent garment is shown as having an outercover 54 component that extends the entire length of the absorbent garment, and forms at least one of the substrates 40 of the front and rear body panels, and also covers the absorbent composite 50 extending along the crotch region of the user. The outercover 54 can be joined to one or more of the absorbent composite and/or body panel substrates. The absorbent garment shown in FIG. 1 is preferably configured as an "open" garment, without any side seams. Instead, the fasteners 42 are secured to the bodyside 10 of the rear body panel 6 and releasably engage the garment side 12 of the front body panel 4, as shown for example in FIG. 13.

Preferably, as shown in FIG. 1, the fasteners 42 are attached to and extend laterally from the outboard edge of the rear body panels from an attachment location 52. It should be understood that the fasteners could be affixed to the front body panels or to both the front and rear body panels. For the purposes of illustration, the right side fastener is shown as being folded in during manufacture, while the left side fastener is shown as being extended outboard during use. Of course, it should be understood that the fastening systems of FIGS. 1 and 5 can be used interchangeably with either embodiment of the body panels shown in those Figures.

Figure 9:
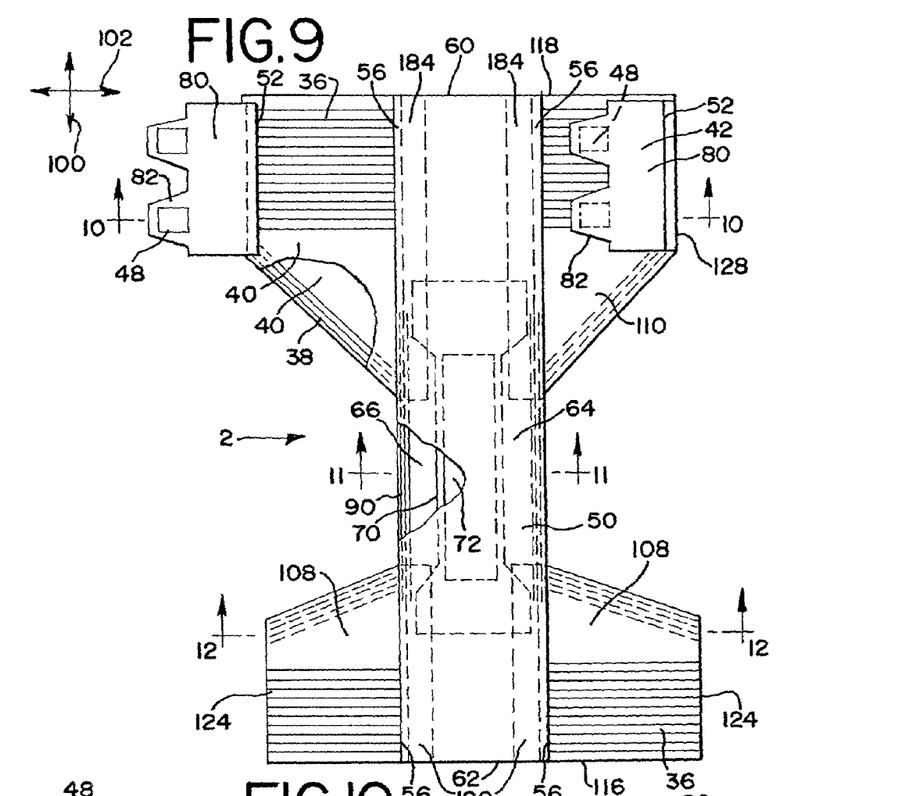
FIG. 9 is a plan view of a third embodiment of an absorbent garment taken from the bodyside thereof.
Figure 10:
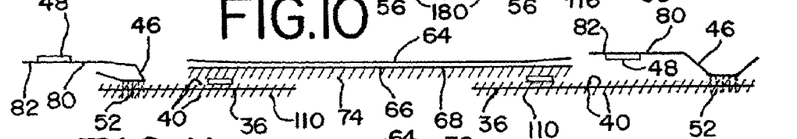
FIG. 10 is a schematic illustration of a cross-sectional view of the absorbent garment taken along line 10—10 in FIG. 9.
Figure 11:
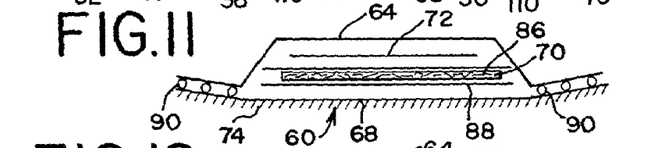
FIG. 11 is a schematic illustration of a cross-sectional view of the absorbent garment taken along line 11—11 in FIG. 9.
Figure 12:
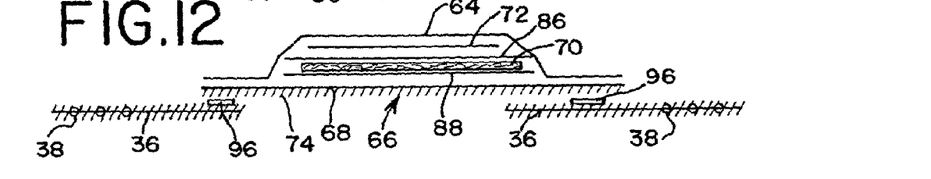
FIG. 12 is a schematic illustration of a cross-sectional view of the absorbent garment taken along line 12—12 in FIG. 9.

In yet another alternative embodiment, shown in FIG. 9, an absorbent composite 50 extends longitudinally along the entire extent of the garment from one end 116 to the other end 118 thereof. A pair of front, side body panels 108 have inboard portions 180 that are secured to opposite side regions of the absorbent composite, preferably on the bodyside thereof, adjacent one end thereof and inboard from a side portion 56 of the absorbent composite. Likewise, a pair of rear, side body panels 110 have inboard portions 184 that are secured to opposite side regions 56 of the absorbent composite, preferably on the bodyside thereof, adjacent the opposite end thereof and inboard from the side portions 56. The body panels 108, 110 extend laterally outward from the absorbent composite and form ear portions having outboard edges 124, 128. It should be understood that the absorbent composite could alternatively be secured to the garment side of the body panels. Preferably, fasteners are fixedly secured to one or both of the body panels and releasably engage one of the body panels as set forth above with respect to the embodiments of FIGS. 1–8.

In yet another embodiment, a body panel is continuous from the rear of the garment through the crotch region to the front of the garment. In such an embodiment, the absorbent composite can be attached to the front, rear and crotch portions of the body panel. In essence, a crotch body panel extends between and connects a front and rear body panel, with the three pieces being made separately or integrally formed as a single unit. The body panel is preferably made of continuous sheets or layers that form the three regions, although it should be understood that separate pieces can be joined, e.g., by bonding, stitching etc., to form the full length body panel.

Referring to FIGS. 1, 2, 5, 6, 9, 10, and 13, each fastener 42 preferably includes a carrier 80 which defines the base 46, with the adhesive element 48, or layer 46, secured thereto. The carrier 80 is preferably configured with a pair of tabs 82, each having an adhesive element 48 applied thereto. It should be understood that the term "element" as used herein means a layer of adhesive material, whether applied directly to the carrier 80 or by way of another substrate. Preferably, the adhesive is a pressure sensitive adhesive, such as that used on various adhesive tapes, e.g., the FT-4933 fastening tape available from Avery International. The carrier 80, or backing material, is preferably made of an elongatable material, or composite, such as that used for the front and rear body panels. In one suitable embodiment, the fastener consists of an adhesive tape used on the Depend® fitted brief, available from Kimberly-Clark Worldwide Corporation, Neenah Wis., the Assignee of this application.

In a preferred embodiment, the adhesive tape is configured with a backing 102, a poly film 104, an adhesive area 48, a non-woven layer 106 and a release tape 108. The adhesive tape is further preferably configured with a finger tab 110, which can be grasped by the user. Preferably, the adhesive area is about $15/16$ inches wide by about 1 and $3/8$ inches long, although other areas would also work.

During the manufacturing process, the adhesive 48 is releasably engaged with the gathered body panel 46 when the body panel is in the unstretched, or non-elongated, condition as the body panel 4, 6 moves through the manufacturing process in a machine direction. As shown in the embodiment of FIG. 5, the adhesive 48 is releasably engaged with the garment side surface 12 of the front body panel 4 inboard from the line of weakness 44. Alternatively, as shown in FIG. 1, the fastener 42 can be initially secured to the rear body panel with the adhesive 48 releasably engaging the bodyside surface 10 of the rear body panel 6.

In use, and referring to FIG. 1, the fasteners 42 are disengaged from the bodyside surface 10 of the rear body panel 6 and the absorbent garment is fitted on the body of the user, with the front body panel 4 extending around the front of the user, and the rear body panel 6 extending around the rear of the user. The absorbent composite 50 extends beneath the crotch region of the user and connects the front and rear body panels 4, 6. Once the garment is appropriately positioned on the user, the user applies the fasteners 42 to the garment side surface 12 of the front body panel 4, thereby securing the rear and front body panels to each other, and the absorbent garment to the user. It should be understood that the fasteners 42 can be releasably engaged with the front body panel 4 before it is fitted on the user and before the body panels, and in particular the front body panel, is elongated, thereby enabling the garment to be pulled on like a pant-type garment. Alternatively, the adhesive elements 48 of the fasteners 42 are releasably engaged with the body panel 4 after the garment is fitted on the user, with the body panel being somewhat elongated prior to the releasable engagement.

Alternatively, as shown in FIG. 5, the absorbent garment 2 is initially pulled on like a pant-type garment. If the garment needs to be removed temporarily, or otherwise adjusted, the user disengages the fasteners 42 and tears the front body panel 4 along one or both of the lines of weakness 44. The user can then reapply the releasably fastener 42, and in particular the adhesive element 48, to the front body panel 4. This process can be repeated (absent the tearing along the line of weakness) as needed.

It should be understood that the adhesive element 18 is preferably the only element releasably engaging the fastener and body panel. However, in various preferred embodiments, the fastener can also be configured with other releasably mechanisms, such as a hook and loop system, buttons, snaps, ties, etc., in combination with the adhesive, which provide auxiliary support for the adhesive element.

Figure 14:
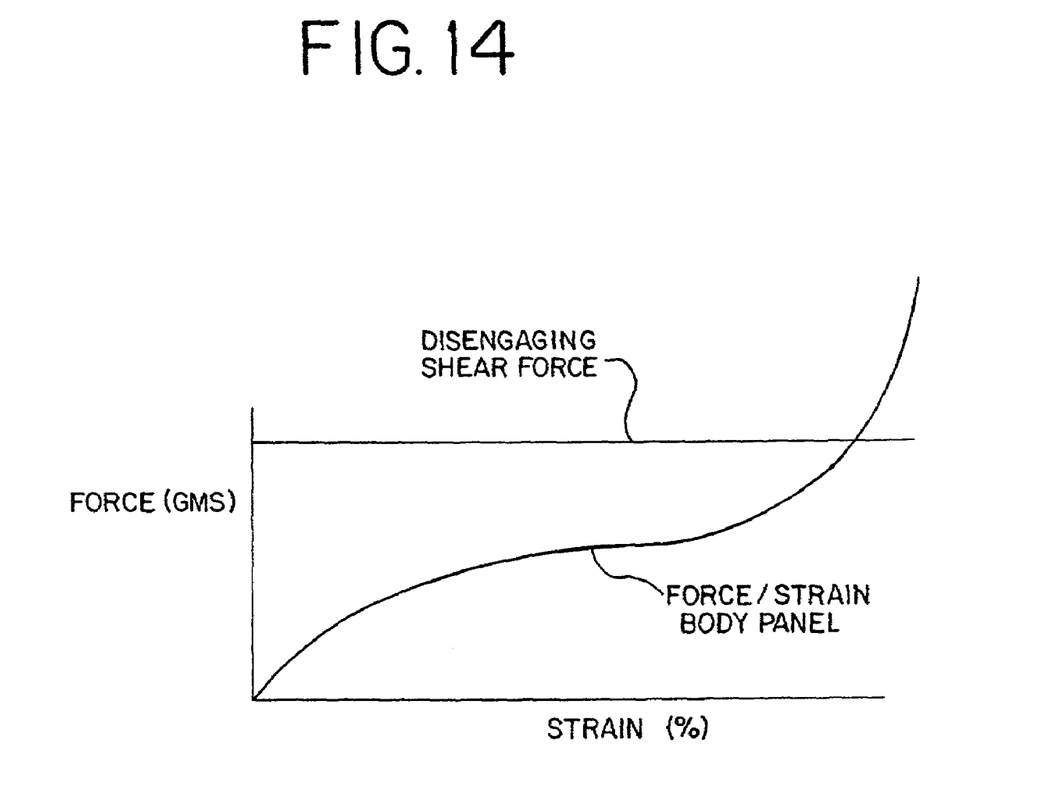
FIG. 14 is an exemplary or theoretical force v. % strain graph of a body panel compared with the disengaging shear force of an adhesive fastener.

Referring to FIG. 14, a force/strain curve illustrates the force to strain relationship of one preferred fibrous elongatable body panel 4, 6, and further the relationship of the force/strain properties of the body panel relative to the shear properties of the adhesive element 48. In particular, as a force is applied to the fastener 42, the force is absorbed by and elongates the elongatable body panel 4, 6. When the force being applied to the elongatable body panel 4, 6 reaches the disengaging shear force required to dislodge or disengage the adhesive fastener 42 from the body panel, adhesive failure will occur. As such, the shear strength of the adhesive attachment, or the disengaging shear force required to disengage the adhesive element, must necessarily be greater than the force needed to elongate the body panel during the normal use of the absorbent garment. Since the body panels 4, 6 are elastically gathered, the body panels 4, 6 can be elongated a considerable amount to conform to the body of the user before the adhesive limit, or disengaging shear force, is reached. Accordingly, the shear to failure of the adhesive attachment does not need to be as high as conventional adhesive fastening systems, and as a result, the force to peel can also be reduced, thereby providing for a fastening system that is refastenable.

In particular aspects of the invention, either or both of the body panels may be composed of a wide range of materials with various basis weights and properties. For example, the body panel material may include knitted or woven fabrics, nonwoven fabrics, polymer films, laminates, and the like, as well as combinations thereof. In various preferred embodiments, the body panel material may be substantially permeable to air or substantially impermeable to air. The body panel material also may be substantially liquid-permeable or substantially liquid-impermeable. In particular arrangements, the body panel material may be substantially non-elastomeric. In other aspects, the body panels can include an elastomeric material that is elastomerically stretchable at least along the lateral article width. Examples of such elastomeric materials can include a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary NBL, SBL, and NSBL materials are described in U.S. Pat. Nos. 5,226,992, 4,981,747, 4,965,122, 5,336,545, 5,414,470, 4,720,415, 4,789,699, 4,781,966, 4,657,802, 4,652,487, 4,655,760, 5,116,662 and 5,114,781, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or MD/CD stretch characteristics, or that are extensible composites.

Preferably, the body panels are breathable, cloth-like, multi-directional nonwoven laminates with stretch and/or extensible properties. In one preferred embodiment, the non-woven layers are pre-necked, preferably between about 10% and about 80%, in the longitudinal direction 100, which provides extensibility in the longitudinal direction with minimum force.

The terms "extensible," "extensibility," and variations thereof as used herein means capable of being extended, and providing a selected elongation when subjected to an applied tensile force. The body panel also is preferably capable of providing a selected, sustained deformation when subjected to an applied tensile force and then allowed to relax for a selected time period beginning immediately after removal of the tensile force. Preferably the sustained deformation is a substantially permanent deformation. The selected elongation and sustained deformation preferably occur at least along the longitudinal direction of the garment, although it should be understood that it also could occur along the lateral direction, or both. Various extensible materials, and other acceptable materials that can be used for the body panels are described for example in U.S. Pat. No. 6,217,563, issued Apr. 17, 2001 to Kimberly-Clark Worldwide, Inc., the same Assignee as the present application, the entire disclosure of which is hereby incorporated herein by reference.

The extensibility of the preferred non-woven material provides an increase in surface area without the retractive force of elastomeric materials. The term "non-woven" web or material, as used herein, means a web having a structure of individual fibers or filaments that are interlaid, but not in an identifiable manner and without the aid of textile weaving or knitting, as in a knitted or woven fabric. In one preferred embodiment, the material provides an elongation of at least about 1 cm when subjected to a tensile force of 11.8 grams per cm. In addition, the body panel preferably provides a substantially permanent deformation of at least about 20% when it is subjected to a tensile force of 19.70 grams per cm and is then allowed to relax under a zero applied stress for a period of 1 minute.

In one preferred embodiment, the front and rear body panels 4, 6 are made of non-woven laminates of two layers or substrates 40 of longitudinally extensible 0.60 osy polypropylene spunbond material with elongated strands of Lycra® elastic 38 sandwiched between the spunbond layers and thereafter adhesively bonded. In certain preferred embodiments, the non-woven materials are made of bonded, continuous fibers, which can help reduce the number of loose fibers available to contaminate the various adhesives used to fasten the garment. The elastics 38 are then allowed to retract so as to gather the necked spunbond material in the lateral direction 102 thereby creating an elastically gathered non-woven body panel with longitudinal extensibility. In this way, the body panel can be elongated in both the longitudinal and lateral direction to conform to the body of the user when the garment is applied thereto. In particular, as the user pulls the garment up over their hips, the non-woven laminate body panels stretch or elongate/retract in the lateral direction 102 while the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto.

Figure 15:
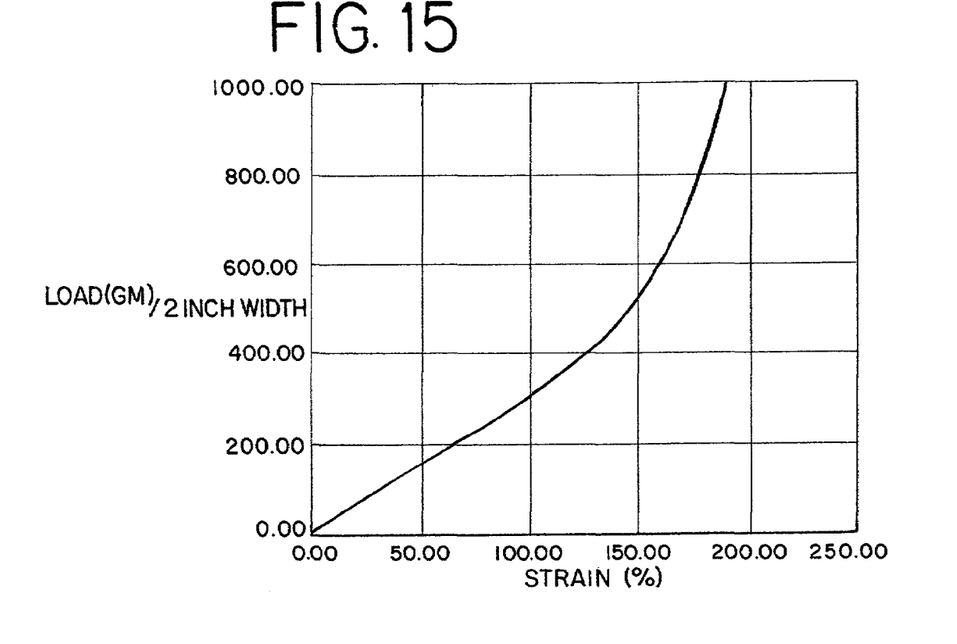
FIG. 15 is a load v. % strain graph of a first body panel material.
Figure 16:
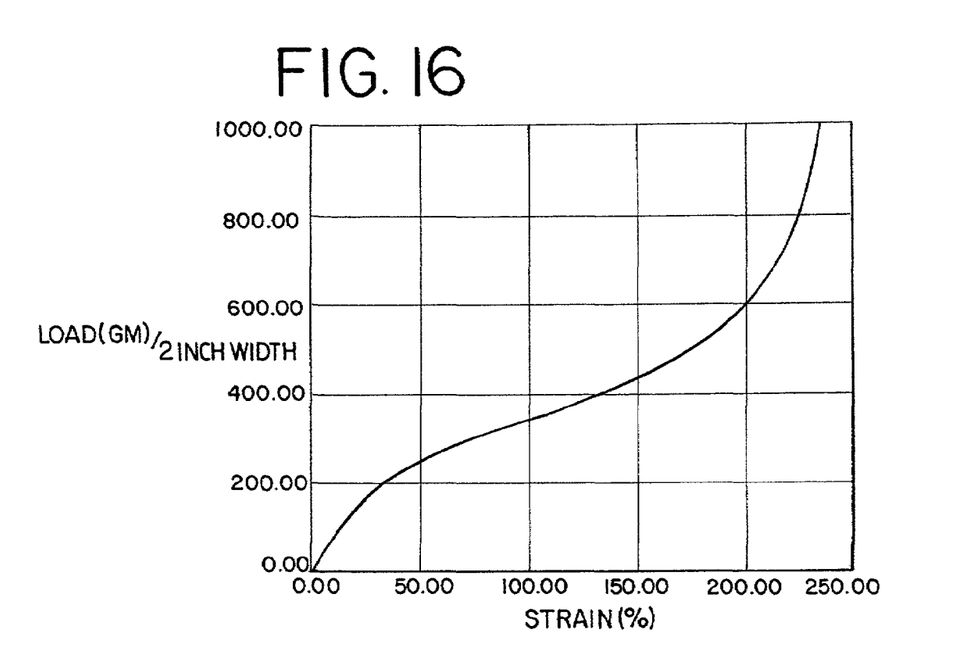
FIG. 16 is a load v. % strain graph of a second body panel material.
Figure 17:
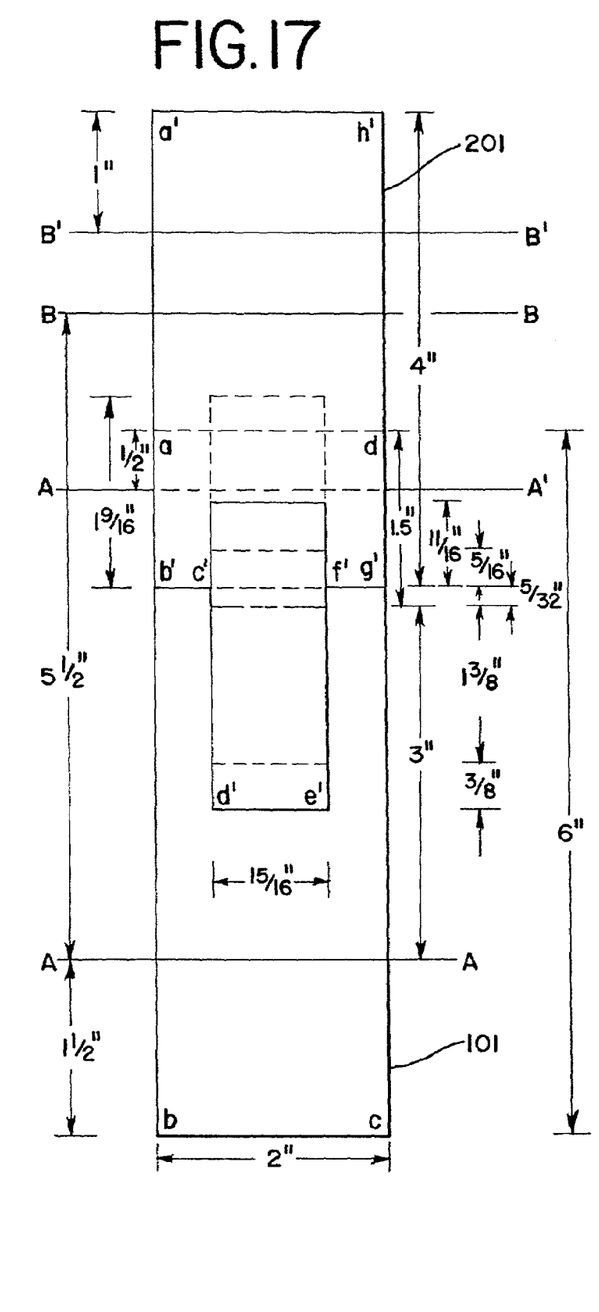
FIG. 17 is a plan view of a test sample of a body panel material and adhesive fastener.
Figure 18:
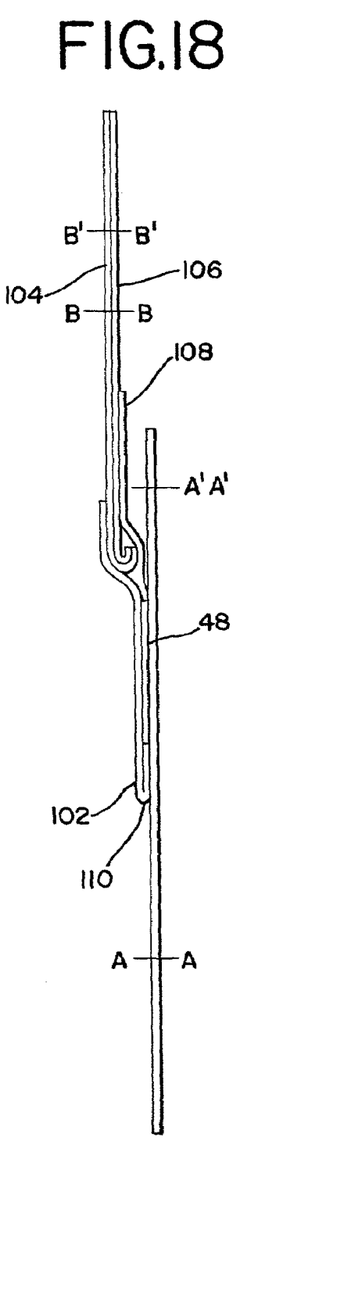
FIG. 18 is a side view of the test sample of the body panel material and adhesive fastener shown in FIG. 17.

Referring to FIGS. 15 and 16 and Tables 1 and 2, various elastically gathered non-woven materials were tested. In particular, tests were run to determine the relative peel and shear strengths of an adhesive fastener secured to an elastically gathered non-woven material, as well as the force/strain relationship of the elastically gathered non-woven material. The samples of the materials were prepared as shown in FIGS. 17 and 18 and as described below.

In particular, the adhesive tape tested was removed from Depend® fitted briefs. Two types of fibrous, gathered nonwoven body panel material were tested: (1) a first material forming the outer cover of Depend® protective underwear and 2) a second material formed from VFL.

In a first test, a tensile test was conducted to obtain a load-strain curve for the two types of stretchable or elongatable fibrous body panel materials. First, a 2 inch wide by 5 inch long specimen is cut from a sheet of material to be tested. The direction of elongation or stretching corresponds to the length direction of the specimen, which is also the test direction. The specimen is clamped between two jaws on a tensile tester (Model: Synergie 200 manufactured by MTS). The initial separation between the jaws is 3 inches. The upper jaw of the tensile tester is activated to travel away from the lower jaw at a speed of 40"/min. The upper jaw stops at an extension of around 6 inches (200% strain). The load- % strain curve is preferably recorded on a computer using TestWorks Version 3.10 software program provided by MTS, although other known and conventional methods for measuring the load v. % strain can be used.

The load v. strain properties of the first and second materials were obtained by conducting the above-referenced tests and are shown in FIGS. 15 and 16 respectively. In both cases, the force remains relatively low until the extension exceeds 6 inches, i.e., 200% of strain. As shown in the curves, the force required to stretch a sample by 100%, i.e., a 3 inch extension, is below 400 grams for both the Depend® protective underwear outer cover and the VFL material. Since the body panel is not typically stretched by 100% during normal wear, 300–400 grams of shear strength of the adhesive tape over a 2 inch wide (59–79 grams/cm) section of the body panel should be sufficient to prevent an adhesive bond failure during normal use and wear for the two fibrous body panel materials tested.

The next tests performed were peel tests of the adhesive fastener secured to the first and second materials. The principles of this test follow ASTM D 1876 00 (Standard Resistance of Adhesives (T Peel Test)). In particular, the distance between the lower and the upper jaws of a tensile tester (Model: Synergie 200 manufactured by MTS) is set at 3½ inches. With reference to FIGS. 17 and 18, the body panel test sample is secured in the lower jaw of the tester along the line A'—A'. The body panel material (abcd in FIG. 17) has dimensions of 2 inches wide by 6 inches long. For a stretchable body panel material, the length direction of the sample corresponds with the stretchable direction of the body panel material. The adhesive tape of the test sample is secured in the upper jaw of the tester along the line B'—B'. The adhesive area of the tape has dimensions of about 15/16 inches wide and about 1⅜ inches long, although it should be understood that other areas could be used.

When preparing a test sample for the peel test, the adhesive fastening tape is first attached to the body panel material with only a slight force applied to the adhesive area to adhere the adhesive fastening tape to the body panel material. With reference to FIG. 17, in the length direction, the distance between one end of the adhesive area and one end of the substrate is about 1.5 inches. In the width direction, the adhesive area is centered onto the body panel material. The adhesive tape is pressed down on the body panel material with a standard 4.5 lb mechanical roller (available from Chemsultants International, a company having offices in Mentor, Ohio) by rolling the roller across the bonded area back and forth one time in the length direction.

When running a peel test, the upper jaw of the tester is activated to travel at a speed of 40 inches/min in the direction away from the lower jaw. The upper jaw stops when the fastening tape and the body panel material are completely separated under peel. The peak load for breaking the adhesive bond in peel is recorded on a computer using TestWorks Version 3.10 software program provided by MTS. The direction of peel was in the elongatable or stretchable direction of the body panel material.

The next tests performed were shear tests of the adhesive tape secured to the first and second body panel materials respectively. The shear tests were conducted to measure the shear strength of the adhesive tape adhered to the stretchable materials. The samples and application of the adhesive tape to the body panel material are the same as described above with respect to the peel test. The direction of the shear test was conducted along the stretchable or elongatable direction of the material. In particular, the distance between the lower and the upper jaws of the tensile tester (Model: Synergis 200 manufactured by MTS) is set at 5½ inches.

With reference to FIG. 17, the body panel material of the test sample is secured in the lower jaw of the tester along the line A—A. The adhesive tape of the test sample is secured in the upper jaw of the tester along the line B—B. The upper jaw of the tester is activated to travel at a speed of 40 inches/min in the direction away from the lower jaw. The upper jaw stops when the adhesive tape and the body panel material are completely separated under shear. The peak load for breaking the adhesive bond in shear is recorded on a computer using TestWorks Version 3.10 software program provided by MTS.

The testing of the peel and shear properties of the adhesive tape were conducted in two stages. In a first stage, the peel strength was recorded after the adhesive tape has been fastened/refastened and peeled as described above five consecutive times. In particular, the first stage consists of the following steps:

1. The adhesive tape is fastened to a stretchable fibrous substrate such as a stretchable body panel as described above.
2. A peel test is conducted to peel the tape off the substrate and the peel strength is recorded.
3. The same tape is refastened to the same area of the substrate used in step 1.
4. Repeat step 2.
5. Repeat steps 3 and 4 for another three times such that a total of five peel tests are performed.

In the second stage, the shear strength of the same adhesive tape and body panel sample used in stage 1 was recorded. Accordingly, the same tape and the same stretchable body panel material used in stage 1 are used in stage 2. Stage 2 consists of the following steps:

1. After five peel tests, the same tape is again refastened, as described above, to the same area of the substrate used in step 1 of stage 1.
2. A shear test is conducted to shear the tape off the substrate and the shear strength is recorded.
3. The same tape is refastened to the same area of the substrate used in step 1.
4. Repeat step 3.
5. Repeat steps 3 and 4 for another three times, such that a total of five shear tests are performed.

Referring to Tables 1 and 2 below, two sets of peel and shear strengths data for each of the body panel materials tested were collected. In each set of data, the first five numbers represent the peel strengths from the first five consecutive peel tests. The next five numbers represent the shear strength from the next five consecutive shear tests.

TABLE 1

Depend ® Tape and Depend ® Protective Underwear Outer Cover

|  | Set 1 (grams) | Set 2 (grams) |
|---|---|---|
| Peel 1 | 366 | 408 |
| Peel 2 | 412 | 341 |
| Peel 3 | 319 | 302 |
| Peel 4 | 300 | 258 |
| Peel 5 | 272 | 284 |
| Shear 1 | 1400 | 1125 |
| Shear 2 | 799 | 676 |
| Shear 3 | 608 | 461 |
| Shear 4 | 549 | 363 |
| Shear 5 | 473 | 352 |

TABLE 2

Depend ® Tape and VFL

|  | Set 1 (grams) | Set 2 (grams) |
|---|---|---|
| Peel 1 | 588 | 600 |
| Peel 2 | 489 | 440 |
| Peel 3 | 440 | 307 |
| Peel 4 | 311 | 231 |
| Peel 5 | 221 | 194 |
| Shear 1 | 576 | 612 |
| Shear 2 | 436 | 426 |
| Shear 3 | 359 | 378 |
| Shear 4 | 330 | 335 |
| Shear 5 | 355 | 386 |

As shown in Tables 1 and 2, both the peel and shear strengths of this particular adhesive tape drop after each peel or shear test because of the increase in adhesive contamination from broken nonwoven fibers. In the case of the Depend® protective underwear outer cover, the peel strength drops from around 400 grams to about 270 grams after five consecutive peel tests. In the case of VFL, the peel strength drops from around 600 grams to about 200 grams. It should be understood that the peel and shear strengths, as referred to herein, refer to the force (grams) associated with the particular adhesive area ($15/16$ inch width by $1 3/8$ long) of the sample used. Accordingly, different size adhesive areas may affect the absolute shear and peel forces exhibited by the fasteners. At the same time, adhesives having varying bonding strengths may affect the absolute shear and peel forces exhibited by different fasteners having the same adhesive areas.

As shown in Table 1, after five consecutive peel tests, the first shear strength is still over 100 grams for the case of Depend® protective underwear outer cover. As indicated in FIG. 15, this amount of force is high enough to stretch the outer cover by about 200% in an area of 2 inches wide, which exceeds the strain during normal use.

As shown in Table 2, after five consecutive peel tests, the first shear strength is still over 570 grams for the case of VFL. As shown in FIG. 16, this amount of force is also high enough to stretch VFL by about 200% in an area of 2 inches wide. Even after five peel tests followed by four shear tests, the fifth shear strength is still over 350 grams for both cases. This amount of force is sufficient to stretch either body panel material by about 100% in an area of 2 inches wide. During normal use and wear of the absorbent garment, the body panel is not typically elongated or stretched over 75% in the area where the adhesive tape is attached. Therefore, the adhesive tape can be refastened several times during normal use and wear without an adhesive bond failure.

In summary, a body panel preferably has a 75% elongation in response to a 300 gms/2 inches (59 grams/cm) force, and more preferably a 100% elongation in response to a 350 grams/2 inches (69 grams/cm) force. In addition, the disengaging shear force of the adhesive is preferably greater than about 300 gms for at least one disengagement, and more preferably preferably is greater than about 300 gms for at least five successive disengagements. In other preferred embodiments, the disengaging shear force of the adhesive is preferably greater than about 500 gms for at least one disengagement, and alternatively greater than about 1000 gms for at least one disengagement. In addition, the disengaging peel force of the adhesive is preferably less than about 650 gms for at least one disengagement, more preferably less than about 450 gms for at least one disengagement and even more preferably less than about 400 gms for at least one disengagement. It should be understood that the peel and shear are measured as a force, and that the area of the adhesive can be altered so as to increase or decrease the peel and shear forces. Accordingly, the areas of the adhesive as described herein are meant to be exemplary and illustrative, rather than limiting. Therefore, adhesive fasteners having greater or lesser areas, with greater or lesser bonding forces relative to the body panel material, can be used that exhibit preferred peel and shear properties relative to the elongation properties of the body panel materials.

Referring now to FIGS. 1–12, the absorbent composite 50 has first and second longitudinally opposed terminal end edges 60, 62. The absorbent composite includes a substantially liquid permeable topsheet 64, or liner, and a substantially liquid impermeable backsheet 66, which can be configured as a barrier layer, or as a composite of a cloth-like outer cover 74 and a barrier 68. A retention portion 70 is disposed or sandwiched between the topsheet and the backsheet, which are connected, at least along their peripheral edges. The absorbent composite 50, and in particular the retention portion 70, can be made in many different shapes, including rectangular and hour-glass shapes. It should be understood that the term "absorbent composite" as used herein refers to any material or assembly capable of absorbing liquids or bodily exudates, and may be comprised of a single material or component, for example a retention portion.

In one preferred embodiment, the topsheet 64 and backsheet 66 of the absorbent composite can be minimally attached, e.g. at the peripheral edges, or they can be attached across substantially the entire surface area thereof. The topsheet and backsheet can be Joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. Additional layers, including for example, a surge layer 72, can also be incorporated into the absorbent composite. Preferably, the surge layer does not run the entire length of the absorbent composite and is shorter than the retention portion. In alternative configurations, the topsheet 64 is indirectly joined to the backsheet 64 by affixing the topsheet to intermediate layers, such as the surge layer or retention portion, which in turn is affixed to the backsheet.

Preferably, longitudinally extending elastic elements 90 shown as three, are secured along the sides of the absorbent composite, for example between the top sheet and backsheet.

Preferably, the elastic elements 90 extend along the side margins of the absorbent composite between the body panels and overlap a portion of each body panel 4, 6. The length of the elastic elements is preferably between about 5% and 100% of the length of the absorbent composite. The function of the elastic elements in the side margins of the absorbent composite are to shorten the length of the side margin which pulls the side margins inwardly to form a three-dimensional profile so as to seal or gasket against the body of the user. The elastic elements can be positioned at various laterally spaced positions, depending on the amount of shortening and upward lift desired. The elastic elements can be made of ribbon, films, sprays of elastic, or other elastic configurations know in the art.

The topsheet 64 presents a body-facing surface that is compliant, soft-feeling, and non-irritating to the wearer's skin. Further, the topsheet 64 can be less hydrophilic than retention portion 70, and is sufficiently porous to be liquid permeable, permitting liquid to readily penetrate through its thickness to reach the retention portion. A suitable topsheet layer 64 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 64 is typically employed to help isolate the wearer's skin from liquids held in the retention portion.

Various woven and nonwoven fabrics can be used for topsheet 64. For example, the topsheet may be composed of a meltblown or spunbonded web of the desired fibers, and may also be a bonded-carded-web. The various fabrics can be composed of natural fibers, synthetic fibers or combinations thereof.

The topsheet fabrics may be composed of a substantially hydrophobic material, and the hydrophobic material may optionally be treated with a surfactant or otherwise process to impart a desired level of wettability and hydrophilicity. In a particular embodiment of the invention, the topsheet 64 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various embodiments, as described below, the topsheet can be made of extensible materials, as described with respect to the body panels and backsheet. For example, the topsheet can be prenecked for extensibility.

The backsheet 66, and in particular the barrier 68, is preferably liquid impermeable, but may be liquid permeable, e.g., when a barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In other alternative constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer that may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

The backsheet also can be expandable, for example when it has one or more folds, e.g., one or more z-folds (not shown), or can be both extensible and expandable. The term "expandable" as used herein means to enlarge or to increase the extent or area, lateral and/or longitudinal, thereof, e.g., by unfolding one or more folds. Likewise, the term "elongated," "elongatable," and variations thereof, broadly means to enlarge or increase the extent or length or width thereof, for example by unfolding, stretching or deforming or other similar actions.

The retention portion 70 has laterally opposed side edges and preferably can be made of a single or dual layer of absorbent material, which can be any material that tends to swell or expand as it absorbs exudates, including various liquids and/or fluids excreted or exuded by the user. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate 86 is disposed adjacent the retention portion. Alternatively, a lower tissue substrate 88 can be disposed adjacent an opposite side of the retention portion, or the tissue can completely envelope the retention position.

In one preferred embodiment, the retention portion 70 is preferably made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

Figure 4:
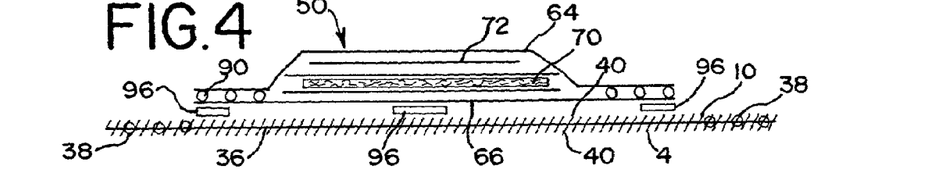
FIG. 4 is a schematic illustration of a cross-sectional view of the absorbent garment taken along line 4—4 in FIG. 1.

Referring to FIGS. 1, 4, 5, 6, 9, 10 and 12, the garment side of the absorbent composite 50, and in particular, the outer, garment side surface of the backsheet 66, is secured to the bodyside surface of the longitudinally opposed crotch ends of the first and second body panels 4, 6, or to the side body panels 108, 110. It should be understood that the absorbent composite can be secured using any of the methods of attachment described above, including for example and without limitation, adhesive bonds, sonic bonds, thermal bonds, pinning, stitching or other attachment techniques known in the art, as well as combinations thereof. Moreover, various portions, patterns, and surface areas of the absorbent garment can be secured to the body panels, as shown for example in U.S. patent application Ser. No. 10/053,251, filed Nov. 7, 2001 and assigned to Kimberly-Clark Worldwide, Inc., the entire disclosure of which is hereby incorporated herein by reference. For example, as shown in FIGS. 4 and 6, the absorbent composite 50 is secured to the body panel 4 along three longitudinally extending attachment locations 96.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An absorbent garment comprising:
   a body panel comprising a liquid permeable, non-woven material, wherein said non-woven material is elastically gathered at least in a fastener engaging region and is elongatable between a non-elongated condition and an elongated condition in response to an application of a tensile force, wherein said body panel comprises a laminate of non-woven substrates with a plurality of elastic elements disposed therebetween in said fastener engaging region, wherein said body panel is elongatable at least 50% between said non-elongated condition and said elongated condition upon said application of said tensile force; and
   a fastener comprising an adhesive directly, releasably engaging said elastically gathered non-woven material at said fastener engaging region, wherein said fastener is releasably disengageable from said elastically gathered non-woven material of said body panel at said fastener engaging region in response to an application of a disengaging shear force, wherein said disengaging shear force is greater than said tensile force.

2. The absorbent garment of claim 1 wherein said fastener is releasably disengageable with said elastically gathered non-woven material at least one time upon the application of at least one disengaging shear force, wherein said at least one disengaging shear force is greater than said tensile force.

3. The absorbent garment of claim 2 wherein said fastener is successively releasably disengagin with said elastically gathered non-woven material at least five times upon the successive application of at least five disengaging shear forces, wherein each of said at least five disengaging shear forces are greater than said tensile force.

4. The absorbent garment of claim 1 wherein said body panel is elongatable at least 75% between said non-elongated condition and said elongated condition upon said application of said tensile force.

5. The absorbent garment of claim 1 wherein said tensile force is less than about 59 g/cm.

6. The absorbent gannent of claim 1 wberein said tensile force is less than about 79 g/cm.

7. The absorbent garment of claim 1 wherein said body panel is elongatable at least 100% between said non-elongated condition and said elongated condition upon said application of said tensile force.

8. An absorbent garment comprising:
   a body panel comprising a liquid permeable, non-woven material, wherein said non-woven material is elastically gathered at least in a fastener engaging region and is elongatable between a non-elongated condition and an elongated condition in response to an application of a tensile force, wherein said body panel is elongatable at least 50% between said non-elongated condition and said elongated condition upon said application of said tensile force; and
   a fastener comprising an adhesive directly, releasably engaging said elastically gathered non-woven material at said fastener engaging regigon, wherein said fastener is releasably disengageable from said elastically gathered non-woven material of said body panel at said fastener engaging region in response to an application of a disengaging shear force, wherein said disengaging shear force is greater than said tensile force;
   wherein said body panel comprises a first body panel having a terminal waist edge and a terminal crotch edge and further comprising a second body panel having a terminal waist edge and a terminal crotch edge, wherein said terminal crotch edges of said first and second body panels are longitudinally spaced, wherein said fastener is fixedly attached to said second body panel.

9. The absorbent garment of claim 8 wherein said second body panel comprises an elastically gathered, liquid permeable, non-woven material.

10. The absorbent garment of claim 1 further comprising an absorbent composite connected to said body panel, wherein said absorbent composite comprises a liquid impermeable backsheet, a liquid permeable top sheet and a retention portion sandwiched between said backsheet and said topsheet.

11. The absorbent garment of claim 1 wherein said disengaging shear force is greater than about 300 grams.

12. The absorbent garment of claim 1 wherein said disengaging shear force is greater than about 500 grams.

13. The absorbent garment of claim 1 wherein said disengaging shear force is greater than about 1000 grams.

14. An absorbent garment comprising;
   a body panel comprising a liquid permeable, non-woven material wherein said non-woven material is elastically gathered at least in a fastener engaging region and is elongatable between a non-elongated condition and an elongated condition in response to an application of a tensile force, wherein said body panel is elongatable at least 50% between said non-elongated condition and said elongated condition upon said application of said tensile force, wherein an entire thickness of said body panel is liquid permeable at least in said fastener engaging region; and a fastener comprising an adhesive directly, releasably engaging said elastically gathered non-woven material at said fastener engaging region, wherein said fastener is releasably disengageable from said elastically gathered non-woven material of said body panel at said fastener engaging region in response to an application of a disengaging shear force, wherein said disengaging shear force is greater than said tensile force.

15. The absorbent garment of claim 14 wherein said entire thickness of an entirety of said body panel is liquid permeable.

16. The absorbent garment of claim 9 wherein said longitudinally spaced crotch edges form a gap therebetween, and further comprising an absorbent composite bridging said gap and connected to said first and second body panels.

* * * * *